United States Patent [19]

Sanchez

[11] 4,434,293

[45] Feb. 28, 1984

[54] TETRAHYDROTHIOPHENE DERIVATIVES AND METHODS OF PREPARATION

[75] Inventor: Robert A. Sanchez, La Jolla, Calif.

[73] Assignee: American Hoechst Corporation, Somerville, N.J.

[21] Appl. No.: 290,390

[22] Filed: Aug. 5, 1981

Related U.S. Application Data

[63] Continuation-in-part of Ser. No. 116,094, Jan. 28, 1980, abandoned.

[51] Int. Cl.³ .................. C07D 333/32; C07D 333/34; C07D 495/12
[52] U.S. Cl. ........................................ 549/17; 549/62; 424/275; 48/195; 48/196 R
[58] Field of Search ..................................... 549/62, 17

[56] References Cited

U.S. PATENT DOCUMENTS

| | | | |
|---|---|---|---|
| 2,400,436 | 5/1946 | Patterson et al. | 549/62 |
| 2,532,612 | 12/1950 | Doumani | 549/62 X |
| 3,096,342 | 7/1963 | Krespan | 549/17 |
| 3,357,996 | 12/1967 | Cobb | 260/332.1 |
| 4,020,170 | 4/1977 | Ouweland et al. | 549/62 |
| 4,134,901 | 1/1979 | Ouweland et al. | 549/62 |

OTHER PUBLICATIONS

C.A., 76, (1972), 72393x; Tolstikov et al.
C.A., 87, (1977), 87-5592a; Novitskaya et al.
C.A., 9th Coll. Index for vols. 76-85, 1972-1976, (1978), p. 38366cs.
OAE, "Organic Chemistry of Sulfur", (1977), Plenum Press, N.Y., pp. 572-573.
Sanchez, Synthesis; Communications; (1982), Feb., pp. 148-149.

Primary Examiner—Joseph Paul Brust
Attorney, Agent, or Firm—Natalie Jensen

[57] ABSTRACT

The novel compounds cis-3-hydroxy-4-mercaptotetrahydrothiophene (I) and octahydrodithieno(3,4-b:3',4'e) 1,4-dithin (II) are prepared from 1,4-dithiothreitol and 1,4-dithioerythritol respectively. (I) has utility as an antibacterial agent. (II) has utility as an odorant.

7 Claims, No Drawings

TETRAHYDROTHIOPHENE DERIVATIVES AND METHODS OF PREPARATION

This is a continuation-in-part of Ser. No. 116,094, filed Jan. 28, 1980, now abandoned.

DESCRIPTION OF THE INVENTION

The present invention relates to novel tetrahydrothiophene derivatives. More particularly, the present invention relates to compounds represented by the formulas

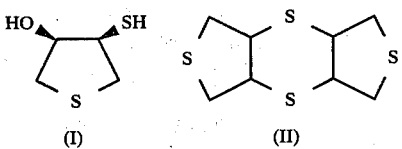

and to processes for the preparation of such compounds.

The subject compound of formula (I), namely cis-3-hydroxy-4-mercaptotetrahydrothiophene, exhibits antimicrobial activity against a variety of microorganisms. For example, the compound exhibits antibacterial activity against pseudomonas aeroginosa p0 pseudomonas fragi,
pseudomonas stutzeri,
pseudomonas fluorescens,
proteus vulgaris,
norcardia erythropolis, and
arthobacter sialophilus.

In view of the aforementioned activity, the compound of formula (I) has a variety of industrial applications. For example, the compound may be employed to flush distilled water systems to eliminate the presence of various species of pseudomonas that commonly contaminate industrial water supplies. The compound may also be added to bottled reagents to minimize contamination due to bacterial growth. Like most compounds containing free sulfhydryl groups, the compound of formula (I) possesses a somewhat unpleasant odor. Accordingly, use of the compound appears to be best suited to closed-systems such as those described above. In all applications, the compound is employed in amounts sufficient to minimize or inhibit the growth of contaminating microorganisms. Such amounts will be readily apparent to those skilled in the art to which the invention pertains from microorganism susceptibility data presented infra.

The subject compound of formula (II), namely octahydrodithieno(3,4b:3′,4′-e)1,4-dithin, is extremely useful as an odorant in natural gas. For example, incorporation of 1 to 2 ppm of the compound in methane produces an extremely odorous gas which is readily detected by persons exposed to same thereby warning of the potential accumulation of explosive and asphyxiating vapors.

The process for the preparation of the compound of formula (I) is schematically illustrated below:

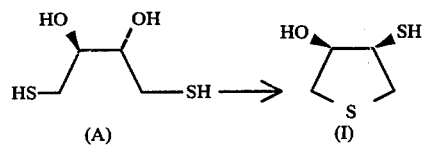

In the above depicted reaction, cis-3-hydroxy-4-mercaptotetrahydrothiophene (I) is prepared by treating 1,4-dithiothreitol (A) with a strong inorganic acid. Typically, this treatment is conducted in the absence of a solvent at temperatures in the range of about 25° to 100° C., preferably at 90° to 100° C., for about from 30 minutes to 24 hours, preferably about 20 to 60 minutes.

The process for the preparation of the compound of formula (II) is schematically illustrated below:

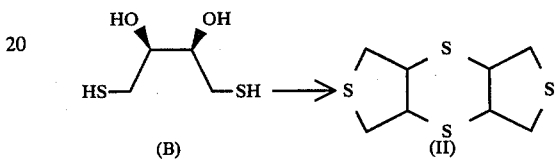

In the above depicted reaction, octahydrodithieno(3,4-b:3′, 4′-e)1,4-dithin (II) is prepared by treating 1,4-dithioerythritol (B) with a strong acid in aqueous media. Typically, this treatment is conducted at temperatures in the range of 25° to 100° C. (preferably at 90° to 100° C.) for about from 5 minutes to 24 hours preferably about, 20 minutes to 2 hours.

Suitable inorganic acids that may be employed in the above described processes include sulfuric acid, phosphoric acid and hydrochloric acid. The use of hydrochloric acid is preferred.

The structure of cis-3-hydroxy-4-mercaptotetrahydrothiophene has been established by elemental microanalysis, spectroscopy (IR, NMR, MS), conversions to an O,S-diacetate ester and an O,S-cyclic carbonate ester, and desulfurization with Raney nickel to 2-butanol.

The structure of octahydrodithieno (3,4-b:3′,4′-e) 1,4-dithin has been established by elemental microanalysis and by spectroscopy (IR, NMR, MS).

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE I

Preparation of cis-3-hydroxy-4-mercaptotetrahydrothiophene

A solution of 40.0 g (0.26 moles) of 1,4-dithiothreitol in 400 mL of concentrated hydrochloric acid in a loosely covered flask is heated in a steam bath. After 40 minutes the resulting clear solution is diluted with 400 mL of water and extracted four times with 200 mL portions of ether. The combined extracts are washed with water and brine and then dried over anhydrous MgSO$_4$. The solvent is removed and the resulting oily residue is distilled to yield cis-3-hydroxy-4-mercaptotetrahydrothiophene (11.2 g, 32%): bp 93°–6° C. (0.8 Torr); GC ~98% pure; NMR (CDCl$_3$) δ4.37 (m, 1H, 3—CH), 3.73 (s, 1H, OH), 2.8–3.3 (m, 5H, 4—CH and both $CH_2$), 2.00 (d, J=8 Hz, 1H, SH); IR (neat) 3420 (OH), 2540 cm$^{-1}$ (SH); mass spectrum, m/e (relative intensity) 136 (M$^+$, 35), 118 (M$^+$—H$_2$O, 25), 85 (C$_4$H$_5$S, 87), 60 (C$_2$H$_4$S, 100), 45 (HCS, 70).

Anal. Calcd for C$_4$H$_8$S$_2$O: C, 35.26; H, 5.92; S, 47.07. Found: C, 35.18; H, 5.91; S, 46.98.

EXAMPLE II

Chemical Characterization of cis-3-1-Hydroxy-4-mercaptotetrahydrothiophene.

A. Acetylation:

A mixture of 6.3 g (46.2 mmoles) of cis-3-hydroxy-4-mercaptotetrahydrothiophene, 100 mL of acetic anhydride and 10 mL of triethylamine is kept at 40° C. for 30 minutes. Excess solvents are then removed in vacuo and the residue is partitioned between water and hexane. The hexane phase is washed with water and brine and then dried over anhydrous MgSO$_4$. The solvents are removed under high vacuum at 40° C., leaving an oily residue of the O,S-diacetate ester (8.0 g, 78%): GC ~95% pure; NMR δ5.57 (m, 1H, 3—CH), 3.98 (m, 1H, 4—CH), 2.7–3.4 (m, 4H, both CH$_2$), 2.37 (s, 3H, AcS), 2.07 (s, 3H, AcO); IR (neat) 1743 (OAc), 1693 cm$^{-1}$ (SAc).

Anal. Calcd for C$_8$H$_{12}$O$_3$S$_2$: C, 43.61; H, 5.49; S, 29.11.

Found: C, 43.71; H, 5.59; S, 28.89.

B. Carboxylation.

A mixture of 1.0 g (7.34 mmoles) of cis-3-hydroxy-4-mercaptotetrahydrothiophene and 1.5 g (9.3 mmoles) of carbonylidiimidazole is heated for 5 minutes in a steam bath. Thereafter the mixture is cooled and partitioned between 10 mL of cold 2M HCl and 40 mL of ether. The ether phase is washed with brine and dried over anhydrous MgSO$_4$. Evaporation of the ether yields 0.95 g of a crude product which is recrystallized from chloroform-hexane to yield the crystalline; cyclic carbonate ester (0.85 g, 71%): GC homogenous, mp 55°–6° C., NMR (CDCl$_3$) δ5.30 (m, 1H, 3—CH), 4.38 (m, 1H, 4—CH), 3.18 (m, 4H, both CH$_2$); IR (KBr pellet) 1710 cm$^{-1}$ (C=O); Anal. Calcd for C$_5$H$_6$O$_2$S$_2$: C, 37.02; H, 3.73; S, 39.53. Found: C, 37.06; H, 3.68; S, 39.41.

C. Desulfurization.

A mixture of 1.0 g (7.34 mmoles) of cis-3-hydroxy-4-mercaptotetrahydrothiophene and 15 g of Raney nickel (wet paste) in 10 mL of water is heated at 70° C. for 3 hours with frequent agitation. The nickel then filtered off and washed with water. The combined filtrates are saturated with NaCl and then extracted with ether. The extracts are dried over anhydrous magnesium sulfate and then carefully stripped of solvent by distillation, leaving a residue of about 0.3 mL. GC at 73° C. demonstrates several components, the major one having a retention time identical to that of authentic 2-butanol. Derivatization with phenyl isocyanate yielded a mixture of products; GC of the mixture at 173° C. demonstrates a major component having a retention time identical to that of authentic 2-butyl phenylcarbamate.

EXAMPLE III

Preparation of octahydrodithieno (3,4-b:3',4'-e)1,4-dithin

A mixture of 35.0 g (0.23 moles) of 1,4-dithioerythritol, 250 mL of concentrated HCl and 250 mL of water is heated to about 75° C. Steam is then passed through the mixture until a total of 800 mL of condensate is collected. The two-phase condensate is extracted with three X 100 mL portions of ether, and the extracts washed with brine and dried over anhydrous CaCl$_2$. The solvent is removed and the oily residue (10.4 g) distilled to yield octahydrodithieno (3,4-b:3',4'-e)1,4-dithin (6.1 g, 23%); bp 58°–60° C. (0.4 Torr); GC ~96% pure; NMR (CDCl$_3$) δ3.48 (m, 4H, CH), 3.20 (M, 8H, CH); IR (neat) 3025, 2965, 2920, 2840 cm$^{-1}$ (CH and CH$_2$); mass spectrum, m/e (relative intensity) 118 (M$^{++}$, 87), 85 (C$_4$H$_5$S, 100), 54 (C$_4$H$_6$, 59), 45 (HCS, 85). The presence of four sulfur atoms in the ions of m/e 118 is confirmed by the expected ratios of isotopic abundances. No parent ion is observed at m/e 236. Anal. Calcd for C$_8$H$_{12}$S$_4$: C, 40.64; H, 5.12; S, 54.22. Found: C, 39.66; H, 5.10; S, 55.36.

EXAMPLE IV

The following example illustrates the antibacterial utility of cis-3-hydroxy-4-mercaptotetrahydrothiophene.

The antibacterial susceptibility testing described herein is based on accepted procedures described in Chapter 37 of the Manual of Clinical Microbiology, Williams and Wilkins Company, Baltimore, Maryland, pp. 299–307 (1970).

PROCEDURE

Cultures of each organism being tested were grown in trypticase soybroth and then inoculated at 1:1000 dilution into tubes containing a specified amount of broth and varying concentrations of antibacterial agent, i.e., 3-hydroxy-4-mercaptotetrahydrothiophene (I). Following 18 hours incubation at 30° C., the tubes were examined for the presence or absence of growth vs. a control tube containing no antibacterial agent. Tubes exhibiting no visible growth were placed onto trypticase soy agar and incubated for 18 hours at 30° C. to ascertain whether the antibacterial effect was bacteriocidal or bacteriostatic. The results of the susceptibility testing are presented in the following table.

| | | Concentration of cis-3-hydroxy-4-mercaptotetrahydrothiophene | | | | |
|---|---|---|---|---|---|---|
| Organism | Control | 500 ug/ml | 1 mg/ml | 2 mg/ml | 3 mg/ml | 4 mg/ml |
| 1 | + | + | + | +/− | − | − |
| 2 | + | + | + | + | − | − |
| 3 | + | + | + | − | − | − |
| 4 | + | + | + | − | − | − |
| 5 | + | + | + | − | − | − |
| 6 | + | + | +/− | − | − | − |
| 7 | + | + | + | +/− | − | − |
| 8 | + | + | + | − | − | − |
| 9 | + | + | + | − | − | − |
| 10 | + | + | + | − | − | − |
| 11 | + | + | + | − | − | − |
| 12 | + | + | + | − | − | − |
| 13 | + | + | + | − | − | − |

+ = visible growth;
+/− = very light visible growth;
− = no visible growth.

1=Pseudomonas aeroginosa; 2=Proteus vulgaris; 3=Pseudomonas fluorescens; 4=Pseudomonas fragi (ATCC #4973); 5=Pseudomonas stutzeri (ATCC #19154); 6=Norcardia erthropolis (ATCC #4277); 7=Norcardia erythropolis (ATCC #17895); 8=Arthrobacter sialophilus; 9=Pseudomonas stutzeri (ATCC #11607); 10=Pseudomonas stutzeri (ATCC #17587); 11=Pseudomonas stutzeri (ATCC #17588);

12 = Pseudomonas stutzeri (ATCC #17591);
13 = Pseudomonas stutzeri (ATCC #17832).

Organisms susceptible to a concentration of 2 mg/ml cis-3-hydroxy-4-mercaptotetrahydrothiophene (I) (i.e., organisms exhibiting no visible growth) all exhibit visible growth when plated onto trypticase soy agar indicating that the antibacterial effect of (I) at this concentration is bacteriostatic.

All organisms are susceptible to a concentration of 3 mg/ml cis-3-hydroxy-4-mercaptotetrahydrothiophene (I). At 3 mg/ml, organisms numbered 6, 7, 11 and 12 exhibit no visible growth when plated onto trypticase soy agar. At a concentration of 4 mg/ml, the above enumerated organisms as well as organisms numbered 11 and 12 exhibit no visible growth when plated onto trypticase soy agar, indicating that the antibacterial effect of (I) for Norcardia erythropolis and most strains of Pseudomonas stutzeri at these concentrations is bacteriocidal.

What is claimed is:

1. Octahydrodithieno (3,4-b:3',4'-e)1,4-dithin.
2. A process for preparing cis-3-hydroxy-4-mercaptotetrahydrothiophene which comprises:
   (a) treating 1,4-dithiothreitol with a strong inorganic acid; and
   (b) recovering cis-3-hydroxy-4-mercaptotetrahydrothiophene from the reaction mixture of step (a).
3. A process according to claim 2 wherein step (a) comprises treating 1,4-dithiothreitol with hydrochloric acid.
4. A process according to claim 2 wherein said treatment is conducted in the absence of a solvent at a temperature 25° to 100° C. for a period of 30 minutes to 24 hours.
5. A process for preparing octahydrodithieno (3,4-b:3',4'-e) 1,4-dithin which comprises:
   (a) treating 1,4-dithioerythritol with a strong inorganic acid in aquesus media; and
   (b) recovering octahydrodithieno (3,4-b:3',4'-e)1,4-dithin from the reaction mixture of step (a).
6. A process according to claim 5 wherein step (a) comprises treating 1,4-dethioerythritol with hydrochloric acid.
7. A process according to claim 5, wherein treatment is conducted at a temperature of 25° to 100° C. for a period of 5 minutes to 24 hours.

* * * * *